United States Patent

Abrahamson et al.

Patent Number: 5,649,969
Date of Patent: Jul. 22, 1997

[54] METHOD AND APPARATUS FOR CALCULATING AND MONITORING THE IMPEDANCE OF AN IMPLANTED PACEMAKER LEAD FROM A SURFACE ECG OF A PACEMAKER PULSE

[75] Inventors: Hans Abrahamson, Stockholm; Hans Andersen, Hassselby, both of Sweden

[73] Assignee: Pacesetter AB, Solna, Sweden

[21] Appl. No.: 694,940

[22] Filed: Aug. 9, 1996

[30] Foreign Application Priority Data

Jun. 20, 1996 [SE] Sweden .................................. 9602440

[51] Int. Cl.⁶ ...................................................... A61N 1/08
[52] U.S. Cl. ............................................... 607/28; 128/697
[58] Field of Search ........................... 128/697; 607/6–8, 607/11, 28

[56] References Cited

U.S. PATENT DOCUMENTS

| | | |
|---|---|---|
| 4,140,131 | 2/1979 | Dutcher et al. . |
| 4,899,750 | 2/1990 | Ekwall ................................. 607/28 |
| 5,385,576 | 1/1995 | Noren et al. ........................... 607/6 |
| 5,423,871 | 6/1995 | Hoegnelid et al. . |
| 5,431,692 | 7/1995 | Hansen et al. . |

FOREIGN PATENT DOCUMENTS 0360551  3/1990  European Pat. Off. .

Primary Examiner—William E. Kamm
Assistant Examiner—George R. Evanisko
Attorney, Agent, or Firm—Hill, Steadman & Simpson

[57] ABSTRACT

A method and apparatus for calculating and monitoring the impedance of an implanted pacemaker lead, and in particular to such a method and apparatus for monitoring the impedance to determine whether a lead fault, such as a lead rupture or a lead dislocation, has occurred. In order to avoid reprogramming the implanted pacemaker to deliver a pulse having known parameters in order to permit an impedance measurement to be made, the method and apparatus operate on the basis of the system formed by the pulse generator, the electrode leads and body tissue being considered to behave as an RC circuit, with the pulse generator emitting an ideal square wave pulse which then exhibits an exponential decay in the body tissue having a decay time constant associated therewith. From surface ECG measurements, the decay time constant is estimated, and since the capacitance of the pulse generator is known, the lead impedance can then be calculated. A determination can then be made whether the calculated lead impedance deviates from the nominal lead impedance to such an extent that a malfunction is assumed to be present.

10 Claims, 1 Drawing Sheet

5,649,969

METHOD AND APPARATUS FOR CALCULATING AND MONITORING THE IMPEDANCE OF AN IMPLANTED PACEMAKER LEAD FROM A SURFACE ECG OF A PACEMAKER PULSE

BACKGROUND OF THE INVENTION

1. Field of the Invention

The present invention is directed to a method and apparatus for calculating and monitoring the impedance of an implanted pacemaker lead, and in particular to such a method and apparatus for monitoring the impedance to determine whether a lead fault, such as a lead rupture or a lead dislocation, has occurred.

2. Description of the Prior Art

In general, an implanted cardiac stimulator, such as a pacemaker, includes a pulse generator, and associated electronics, contained in a hermetically sealed housing, and an electrode lead system including one or more electrode cables. Each electrode cable has one or more electrodes disposed at or near a distal end of a sheath of insulating material surrounding an electrical conductor, and has a proximal end with an electrical connector which is connectable to the pulse generator housing at a connector jack located on the housing. Typically, each electrode cable is implanted by advancing the electrode cable through a vein and into the atrium or ventricle of the heart which is to be stimulated. Usually, it is desirable that the electrode or electrodes carried at the distal end of the cable be located in the heart at a relatively specific position, in order to achieve a desired stimulation therapy. The pulse generator housing is implanted at a location remote from the distal end or ends of the electrode cable or cables, typically at a sub-clavial or an abdominal location.

In order for the desired pacing therapy to be administered by the pacemaker, it is important that a complete (closed) electrical circuit be present, including the pulse generator and the electrode cable or cables attached thereto. It is common to employ the pacemaker housing as an indifferent electrode, so that a return path for current, following delivery of a stimulation pulse, exists between the stimulation electrode and the housing through body tissue. Interruptions or modifications of this complete circuit can occur, for example, if the electrical connection at the housing jack becomes contaminated with body fluid or otherwise becomes loosened, or if a rupture occurs at some point along the length of an electrode cable, or if the tip electrode becomes dislodged from its intended placement position in the heart. If any of these malfunctions occurs, it is important to be able to detect the occurrence of the malfunction as soon as possible.

All of the above types of malfunctions will result in a noticeable change in the impedance of the lead system, causing the impedance to deviate noticeably from a "normal" or base value. In order to detect the occurrence of such malfunctions, therefore, it is well-known to include impedance monitoring circuitry in an implantable pacemaker, so as to be able to check periodically to determine whether the lead impedance deviates significantly from the nominal value. If a significant impedance deviation is detected, it is assumed that a malfunction in the lead system has occurred, and some type of warning indicator can be generated.

Since the lead impedance may vary due to a number of different factors, other than the presence of a malfunction, the aforementioned nominal impedance must be associated with a known amplitude, duration and rate of the pacing pulses. In order to detect deviations from this nominal impedance, the pacemaker must at the time of the measurement deliver pacing pulses having the known amplitude, duration and rate. In many instances, however, the amplitude, duration and rate of the pacing pulses which are associated with the nominal impedance may not be the most effective combination for treating the particular cardiac pathology of a person in whom the pacemaker system is implanted. Therefore, if the pacemaker, for administering stimulation therapy, is operating so as to deliver pacing pulses which are different from the pulses associated with the nominal impedance, the pacemaker must be forced to operate temporarily in a mode in which it emits pacing pulses having the amplitude, duration and rate associated with the nominal impedance. During this mode, the aforementioned impedance measurements are made to determine whether deviations from the nominal impedance exist.

In modern pacemakers which are controlled by telemetry by means of an external programmer, a physician or the patient can operate the programmer in order to set the pacemaker to the aforementioned operating mode to permit the impedance measurement to be made. This has the disadvantage, however, of temporarily administering pacing pulses which are different from the pacing pulses that are most effective for treating the patient's particular cardiac pathology, and also requires that the pacemaker, upon completion of the impedance measuring mode, must be reprogrammed to return it to its previous operating parameters.

Examples of implantable cardiac systems which include impedance monitoring of the type described above are disclosed in U.S. Pat. Nos. 4,140,131; 5,423,871 and 5,431,692, and in European Application 0 360 551.

It is also known to identify the presence of a lead malfunction by obtaining a surface electrocardiogram (ECG) of the patient. The "normal" waveform of the ECG is known, and the presence of malfunctions of the type described above will cause artifacts to appear in the waveform which can be recognized on the ECG monitor. For ECG monitoring of lead faults, therefore, it is the ECG waveform itself which is viewed and analyzed, rather than using impedance as the fault-identifying parameter.

SUMMARY OF THE INVENTION

It is an object of the present invention to provide a method and apparatus for calculating and monitoring the impedance of an implanted pacemaker lead using a surface ECG measurement.

The method and apparatus of the invention are based on the perception that the pulse generator, the lead, and the relevant heart tissue can be considered as resembling a resistor and capacitor (RC) network. From a simplified point of view, the pulse generator can be considered as a square wave source having a capacitor at its output terminal, since it is typical for the output circuit of an implanted pulse stimulator to include one or more discrete capacitors. The total impedance of this theoretical circuit is formed by the lead impedance and the impedance of the tissue through which the stimulation current passes. It is assumed that the tissue impedance will not change significantly from impedance measurement to impedance measurement, and therefore if any impedance changes are identified, it is assumed that such changes are due to a change in the lead impedance, i.e., a lead fault. The pulse generator is assumed to generate an "ideal" square wave pulse, before the output capacitor, so that, as is known in general for an RC circuit, the waveform which occurs in the body of the patient will be an exponentially decaying pulse. This exponentially decaying pulse can be registered using a surface ECG recorder. The amplitude decay, as a function of time, u(t), will have the form:

$$u(t) = u_0 e^{-(t/RC)}$$

wherein $u_0$ is the initial amplitude, R is the lead impedance and C is the value of the output capacitance. In accordance with the invention, by means of the surface ECG measurements, the decay time constant $\tau(\tau=RC)$ is estimated, and the lead impedance is then calculated, since the capacitor value is known for a given type of pulse generator. Although the type of pulse generator implanted in a patient will usually be known from written records, it is also common for the external programmer to be able to identify the type of pacemaker with which the programmer is interacting by telemetry.

In order to be able to make the aforementioned estimate using measurements obtained by a surface ECG recorder, at least two measurements (i.e., at least two data points) must be obtained. Conventional surface ECG recorders have, or can be set to have, a high sampling rate and are therefore capable, with appropriate amplification, of sampling a sufficiently large number of data points during the decay phase, in order to be able to accurately estimate the decay time constant by a suitable algorithm, such as by exponential regression analysis. The estimate becomes more accurate as the number of data points increases.

The absolute precision of the aforementioned measurements is affected by the precision of the output capacitor in the pulse generator. In order to identify a lead fault of the type described above, however, it is only necessary to identify variations in the lead impedance, and therefore if a value for the output capacitance is used which may be slightly inaccurate, this same inaccuracy will be the same in each measurement, and therefore it will not effect identification of variations which occur from measurement to measurement. The limiting factor in the precision of the method and apparatus described herein, therefore, is in the external measuring device itself, i.e., the surface ECG recorder.

DESCRIPTION OF THE PREFERRED EMBODIMENTS

Figure 1:
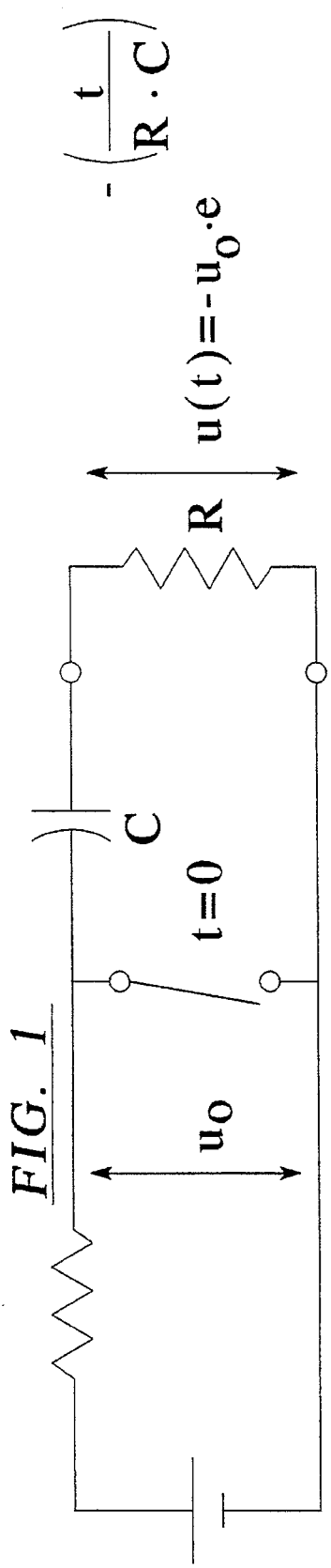
FIG. 1 is a circuit diagram showing a circuit representation of an implanted pacemaker for explaining the method and apparatus of the invention.

As explained above, the invention is based on the recognition that an implanted pacemaker can be viewed, in simplified form, as an RC circuit. Such a circuit is shown in FIG. 1. The circuit includes a voltage source represented as a battery which has a constant voltage $u_0$. The capacitance of the output stage of the pulse generator is represented as a capacitor C (the designation C also representing the capacitance of this capacitor), however, it will be recognized that the capacitor C may, in reality, represent the total capacitance of a number of discrete capacitors. The electrode leads are represented as having an impedance, which is considered to be completely resistive, represented by the resistor R. For completeness, the voltage source having a voltage $u_0$ is shown as being connected in series with an internal resistance, however, since this internal resistance does not play a role in the inventive method and apparatus, it is not otherwise designated.

Consistent with the consideration of the simplified pacemaker circuit diagram as producing an "ideal" square wave preceding the capacitor C, the circuit diagram of FIG. 1 includes a switch which is assumed to be closed at time t=0, and which is opened a short time later. The time during which the switch is closed represents the duration of the "ideal" square wave, and it will have an amplitude equal to $u_0$. In accordance with the conventional analysis of an RC circuit, the brief closing and subsequent opening of the switch produces an exponentially decaying waveform $u(t) = u_0 e^{-(t/RC)}$. As is also known from standard RC circuit analysis, the exponentially decaying waveform has a decay time constant $\tau = RC$.

The output capacitance, represented by the capacitor C, will be known for a given pacemaker. In accordance with the principles of the present invention, the value for the time constant $\tau$ is estimated by taking at least two sampled signals of a surface ECG obtained from the patient after time t=0, i.e., after the switch is closed and then again opened. From the known value for C and the estimated value for $\tau$, the value for R, i.e., the lead impedance, can be calculated as $R = \tau/C$.

Figure 2:
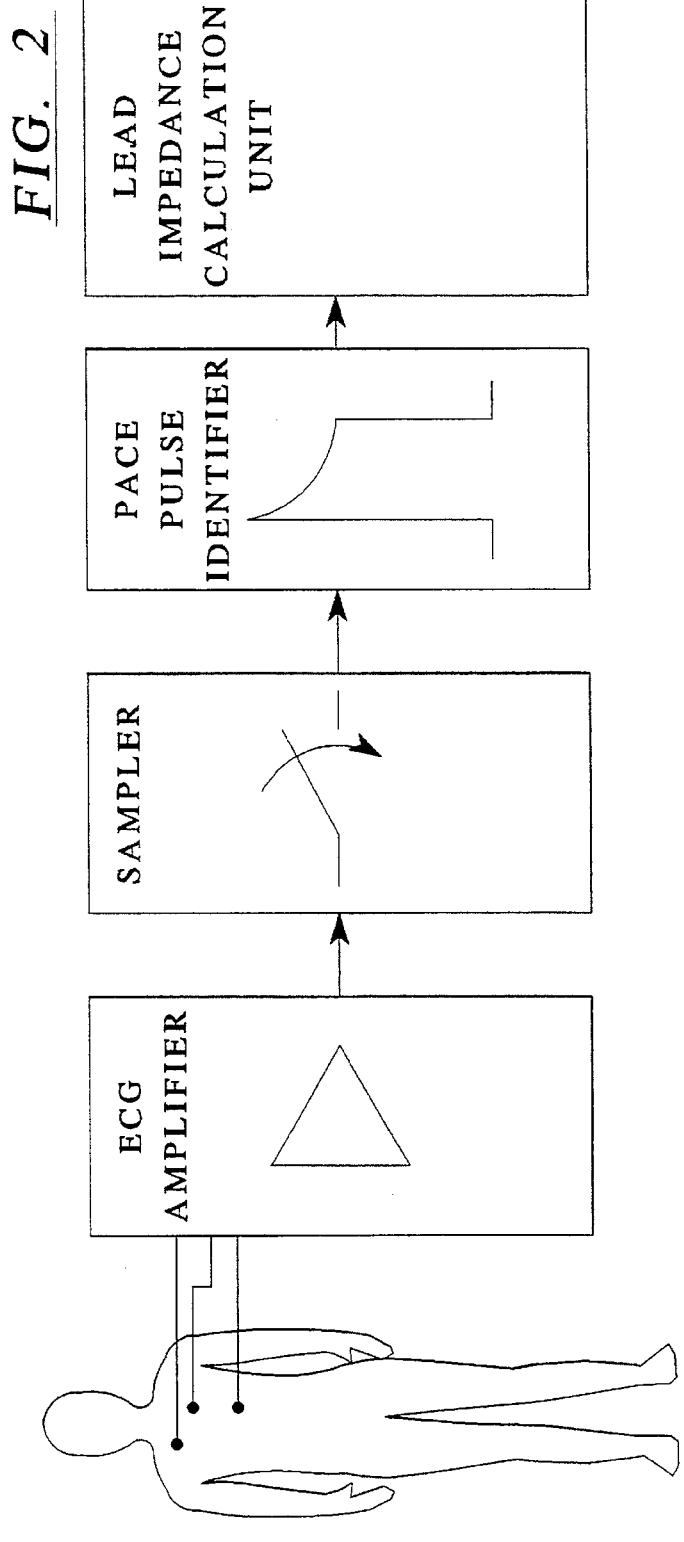
FIG. 2 is a block diagram of an apparatus constructed and operating in accordance with the principles of the present invention.

An apparatus for undertaking the necessary measurements and making an estimate of the value $\tau$, with a subsequent calculation of the lead impedance, is shown in block diagram form in FIG. 2. As shown in FIG. 2, a surface ECG recording system is connected in a known manner to a patient, as represented by the ECG amplifier block. When a stimulation pulse is emitted in the manner described above, an ECG is obtained from the patient with at least two data points being obtained at a suitable sampling rate by a sampler. An estimation of the decay time constant $\tau$ of the waveform following the aforementioned stimulation pulse is made in a pace pulse identifier, and this estimated value is then used to calculate the lead impedance in a lead impedance calculation unit. The output of the lead impedance calculation unit can be used, if desired, to trigger an alarm generator in order to emit an audible or visible alarm signal in the event that the calculated impedance exceeds a predetermined permissible variation. For example, a simple threshold circuit can be used which emits an output signal that triggers an alarm in the event that the impedance exceeds a preset threshold.

Any suitable mathematical procedure can be used to estimate the decay time, however, preferably exponential regression analysis is used for this purpose. The exponential regression analysis is used in accordance with the principles of the invention can proceed according to the following algorithm:

$$\tau = \cfrac{1}{\left( \cfrac{N * \sum_{i=1}^{N} t_i * \ln(u_i) - \sum_{i=1}^{N} t_i * \sum_{i=1}^{N} \ln(u_i)}{N * \sum_{i=1}^{N} (t_i)^2 - \sum_{i=1}^{N} t_i * \sum_{i=1}^{N} t_i} \right)}$$

wherein N is the number of data points, $t_i$ is the time associated with a particular sample and $u_i$ is the voltage associated with a particular sample.

Using this estimated value, the impedance R is calculated in the impedance calculation unit as follows:

$$R = \cfrac{1}{C * \left( \cfrac{N * \sum_{i=1}^{N} t_i * \ln(u_i) - \sum_{i=1}^{N} t_i * \sum_{i=1}^{N} \ln(u_i)}{N * \sum_{i=1}^{N} (t_i)^2 - \sum_{i=1}^{N} t_i * \sum_{i=1}^{N} t_i} \right)}$$

The method and apparatus disclosed herein have the advantage that the lead impedance can be identified from a pacemaker model, without the necessity of undertaking an actual measurement of the lead impedance. A further advantage is that the calculations can be made with only minor interference to the current operating mode of the pacemaker, since it is only necessary that one stimulation pulse be emitted in order to obtain the ECG samples necessary for the invention. Another advantage is that beat-to-beat calculation of the lead impedance is possible, if desired, thereby permitting a physician to monitor the stability of the lead impedance.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for monitoring an electrode lead of a cardiac pacemaker implanted in a subject, said cardiac pacemaker having an output circuit containing a capacitance, comprising the steps of:

pacing a heart of said subject by emitting at least one pacing pulse from said cardiac pacemaker, said pacing pulse after emission exhibiting an exponential decay with an associated decay time;

obtaining at least two surface ECG measurements from said subject during said decay time;

estimating said decay time from said ECG measurements; and identifying an impedance of said electrode lead from a combination of said capacitance and the decay time estimated from the ECG measurements.

2. A method as claimed in claim 1 wherein the step of obtaining at least two surface ECG measurements from said subject comprises sampling an ECG waveform obtained from said subject to obtain a plurality of data points during said decay time.

3. A method as claimed in claim 2 wherein the step of estimating said decay time comprises estimating the decay time from said ECG data points by exponential regression analysis.

4. A method as claimed in claim 3 comprising conducting said exponential regression analysis according to an algorithm:

$$\tau = \cfrac{1}{\left( \cfrac{N * \sum_{i=1}^{N} t_i * \ln(u_i) - \sum_{i=1}^{N} t_i * \sum_{i=1}^{N} \ln(u_i)}{N * \sum_{i=1}^{N} (t_i)^2 - \sum_{i=1}^{N} t_i * \sum_{i=1}^{N} t_i} \right)}$$

wherein $\tau$ is the decay time, N is the number of said data points, $t_i$ is the time at which each data point was obtained, and $u_i$ is the voltage of said stimulation pulse at time $t_i$.

5. A method as claimed in claim 4 wherein the step of identifying an impedance of said electrode lead comprises calculating said impedance according to a relationship:

$$R = \cfrac{1}{C * \left( \cfrac{N * \sum_{i=1}^{N} t_i * \ln(u_i) - \sum_{i=1}^{N} t_i * \sum_{i=1}^{N} \ln(u_i)}{N * \sum_{i=1}^{N} (t_i)^2 - \sum_{i=1}^{N} t_i * \sum_{i=1}^{N} t_i} \right)}$$

wherein R is said impedance and C is said capacitance.

6. An apparatus for monitoring an electrode lead of a cardiac pacemaker implanted in a subject, said cardiac pacemaker having an output circuit containing a capacitance, and said cardiac pacemaker emitting a pacing pulse to a heart of said subject via said electrode lead, said pacing pulse after emission exhibiting an exponential decay with an associated decay time, said apparatus comprising:

means for obtaining at least two surface ECG measurements from said subject during said decay time;

means for estimating said decay time from said ECG measurements; and means for identifying an impedance of said electrode lead from a combination of said capacitance and the decay time estimated from the ECG measurements.

7. An apparatus as claimed in claim 6 wherein said means for obtaining at least two surface ECG measurements comprises means for sampling an ECG waveform from said subject for obtaining a plurality of ECG data points.

8. An apparatus as claimed in claim 7 wherein said means for estimating said decay time comprise means for estimating the decay time from said ECG data points by exponential regression analysis.

9. An apparatus as claimed in claim 8 wherein said means for estimating the decay time from said ECG data points by exponential regression analysis comprises means for conducting said exponential regression analysis according to an algorithm:

$$\tau = \cfrac{1}{\left( \cfrac{N * \sum_{i=1}^{N} t_i * \ln(u_i) - \sum_{i=1}^{N} t_i * \sum_{i=1}^{N} \ln(u_i)}{N * \sum_{i=1}^{N} (t_i)^2 - \sum_{i=1}^{N} t_i * \sum_{i=1}^{N} t_i} \right)}$$

wherein $\tau$ is the decay time, N is the number of said data points, $t_i$ is the time at which each data point was obtained, and $u_i$ is the voltage of said stimulation pulse at time $t_i$.

10. An apparatus as claimed in claim 9 wherein said means for identifying an impedance comprise means for calculating said impedance according to a relationship:

$$R = \cfrac{1}{C * \left( \cfrac{N * \sum_{i=1}^{N} t_i * \ln(u_i) - \sum_{i=1}^{N} t_i * \sum_{i=1}^{N} \ln(u_i)}{N * \sum_{i=1}^{N} (t_i)^2 - \sum_{i=1}^{N} t_i * \sum_{i=1}^{N} t_i} \right)}$$

wherein R is said impedance and C is said capacitance.

* * * * *